United States Patent
Rademacher et al.

(10) Patent No.: US 6,458,746 B1
(45) Date of Patent: Oct. 1, 2002

(54) PLANT GROWTH REGULATING FORMULATIONS

(75) Inventors: Wilhelm Rademacher, Limburgerhof; Karl-Heinrich Schneider, Kleinkarlbach; Reiner Kober, Fussgönheim, all of (DE); Roderick Whitfield King, Deakin; Lewis Norman Mander, Aranda, both of (AU); Richard Persons Pharis, Cochrane (CA)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/720,912
(22) PCT Filed: Jul. 2, 1999
(86) PCT No.: PCT/EP99/04592
§ 371 (c)(1), (2), (4) Date: Jan. 2, 2001
(87) PCT Pub. No.: WO00/02454
PCT Pub. Date: Jan. 20, 2000

(30) Foreign Application Priority Data

Jul. 7, 1998 (EP) .............................................. 98112541

(51) Int. Cl.⁷ .......................... A01N 25/30; A01N 43/12
(52) U.S. Cl. ......................... 504/128; 504/140; 504/297
(58) Field of Search ................................ 504/297, 140, 504/128

(56) References Cited

U.S. PATENT DOCUMENTS

| | | | |
|---|---|---|---|
| 4,799,950 A | 1/1989 | Suzuki et al. | 71/89 |
| 5,163,993 A | 11/1992 | Schafer et al. | 71/89 |
| 5,532,206 A | 7/1996 | Evans et al. | 504/176 |
| 5,767,042 A | 6/1998 | Pharis et al. | 504/297 |
| 6,165,940 A | * 12/2000 | Aven | 504/118 |

FOREIGN PATENT DOCUMENTS

| | | |
|---|---|---|
| GB | 862849 | 3/1961 |
| GB | 930078 | 7/1963 |

OTHER PUBLICATIONS

Thomson "Agricultural Chemicals Book III Miscellaneous Agricultural Chemicals" 1995 Revision pp. 29–36.
Rademacher "Gibberellins" Fungal Biotechnology 1997 pp. 193–205.

* cited by examiner

Primary Examiner—S. Mark Clardy
(74) Attorney, Agent, or Firm—Keil & Weinkauf

(57) ABSTRACT

Plant growth regulating preparations comprising:

(a) 0.1–20 wt. % of a 16,17-dihydro gibberellin of formula (Ia) or (Ib);
(b) up to 99.9 wt. % of a formulation additive selected from:
(b1) the reaction products of triglycerides based on carboxylic acids having 2–30C and ethylene oxide and/or propylene oxide in the presence of a base, and/or
(b2) fatty acid alcohol polyethoxylates;
(c) up to 50 wt. % of an organic solvent;
(d) 0.1–50 wt. % of a formulation auxiliary different from (b1) and (b2);
(e) up to 50 wt. % of additional plant growth regulating compounds can be used in agriculture and horticulture to induce the desired effects on, for example, seed germination and seedling growth, rooting, dormancy, juvenility, maturity and senescence, flowering, abscission of leaves, flowers and fruit, fruit set and development, tuber formation, growth of shoot and root, photoassimilation, control of unwanted plants and senescence of whole plants or single organs. The 16,17-dihydroGA's are used to synergize the biological activity of exogenously supplied gibberellins. Particularly in graminaceous species, the compounds synergize the action of exogenous GA's and can, thus, be used to increase the yield of malt and decrease the amount of time required for the malting process, increase the yield of sugar cane and stimulate germination and seedling development in rice, wheat, barley, oats, rye, maize, sorghum, turf grasses and other plant species.

8 Claims, No Drawings

PLANT GROWTH REGULATING FORMULATIONS

The present invention relates to plant growth regulating preparations comprising
a) 0.1 to 20% by weight of a 16,17-dihydro gibberrelin of general formulae Ia or Ib
b) up to 99.9% by weight of an formulation additive selected from the group consisting of
  b1) the reaction products of triglycerides based on carboxylic acids having 2 to 30 carbon atoms and ethylene oxide and/or propylene oxide in the presence of a base, and/or
  b2) fatty acid esters of sugar alcohol polyethoxylates
c) up to 50% by weight of an organic solvent
d) 0.1 to 50% by weight of a formulation auxiliary different from b1 and b2,
e) up to 50% by weight of additional plant growth regulating compounds.

Furthermore, the present invention relates to the use of the said preparations for the regulation of plant growth.

Numerous plant growth substances are known. Part of these substances are used in agriculture and horticulture in order to induce desired effects, for instance on seed germination and seedling growth
rooting
dormancy
juvenility, maturity and senescence
flowering
abscission of leaves, flowers and fruits
fruit set and development
tuber formation
growth of shoot and root
photoassimilation
control of unwanted plants
senescence of whole plants or single organs

[cf. R. N. Arteca (1996) Plant Growth Substances, Chapman & Hall, New York.]

Gibberellins (GAs) represent one group of plant growth substances. GAs occur naturally in higher plants where they function as phytohormones being involved in the regulation of growth and flowering and numerous other developmental processes. Certain GAs, particularly gibberellic acid or $GA_3$ (ent-3α,10,13-trihydroxy-20-norgiberrell-1,16-diene-7,19-dioic acid 19,10-lactone), are commercially available as fermentation products of the fungus *Gibberella fujikuroi*.

C-16,17-dihydro GAs and related structures have been known since many years. They either occur naturally in higher plants (e.g. $GA_{82}$ and and $GA_{83}$) or in the fungi *Gibberella fujikuroi* (e.g. $GA_2$, $GA_{10}$, $GA_{42}$) and Phaeospheria sp. (e.g. $GA_{82}$).

WO 93/03616 and PCT/AU95/000528 describe for the first time the biological activity of known and newly synthesized 16,17-dihydro GAs and their potential utility for agricultural, horticultural and plant breeding applications. In particular the following biological effects have been described as features of the 16,17-dihydro GAs and/or other ring D-modified GAs:

dwarfing
growth retardation of stem and shoot and/or root
promotion of bud break
flowering
improved fruit quality
inhibition of fruit ripening
prevention of whole plant and/or organ senescence
improved fruit set
control of weed growth
inducing male sterility
retarded bud break
tillering Further details on chemical and biological aspects of distinct 16,17-dihydro or other ring D-modified GAs have been published in the recent scientific literature.

A major obstacle to introduce the ring D-modified gibberellin derivatives described in WO 93/03616 and PCT/AU95/00528 into agricultural and horticultural practice is caused by the costs required to produce these compounds. The production costs are primarily affected by the price of the starting material $GA_3$ [cf. W. Rademacher (1997): Gibberellins, in Fungal Biotechnology, T. Anke (ed.), Chapman & Hall, Weinheim, pp. 193–205].

There thus exists a need in formulations based oh ring modified D-gibberelin derivatives having improved biologicasl activity and thus better economical feasibility.

The object of the present invention was to provide plant growth regulating preparations based on ring D-modified gibberellin derivatives having a very good biological activity, in particular at low application rates.

This object has been achieved with the plant growth regulating formulations as defined in claim 1 and hereinbefore.

Preferred embodiments of the instant invention are set forth in the dependent claims and the following detailed specification.

The C-16,17-dihydro gibberellins (component a) have the chemical formulae Ia or Ib

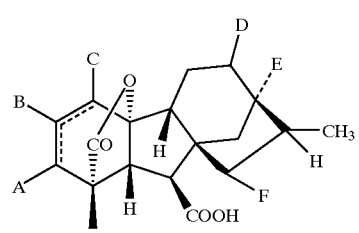

Ia wherein A, B, C, D, E and F independently represent hydrogen atoms or hydroxyl groups and the dotted line represents one optional double bond either between the carbon atoms in position 1 and 2 or between the carbon atoms in positions 2 and 3, and

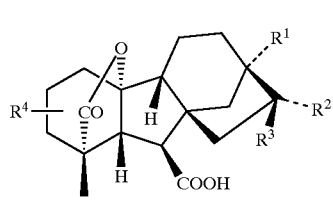

Ib wherein
$R^1$ represents H or OH, OC(=O)$R^5$ or OR$^5$
$R^2$, $R^3$, which may be the same or different, each represent H, F, Cl, Br, lower ($C_{1-6}$) alkyl, lower ($C_{2-6}$) alkenyl, lower ($C_{3-6}$) cycloalkyl, or CH$_2$X (wherein X is F, Cl or Br);

$R^4$ indicates that the A ring may be (i) unfunctionalised, or (ii) contain a 1,2-double bond or 2,3-double bond, or (iii) contain a 3α- or 3β-OH, F, Cl or Br group with or without a 1,2-double bond, or (iv) contain a 1α- or 1β-OH, F Cl or Br group with or without a 2,3-double bond;

$R^5$ represents $C_1$–$C_6$-alkyl.

The following compounds are particularly preferred in the preparation of the inventive preparations:

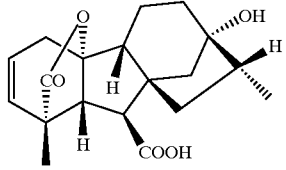

exo-16, 17-dihydro GA₅

II

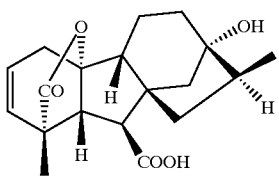

endo-16, 17-Dihydro GA₅

III

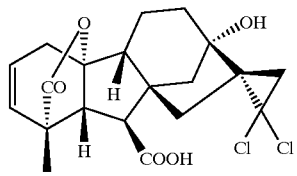

16, 17-Dichloromethano-dihydro-GA₅

IV

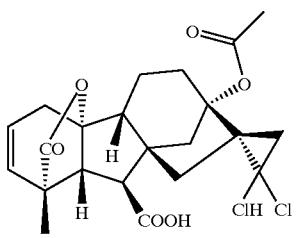

16, 17-Dichloromethano-dihydro-GA₅-13-acetate

V

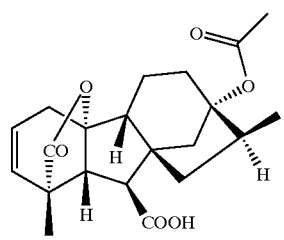

endo-16, 17-Dihydro-GA₅-13-acetate

VI

-continued

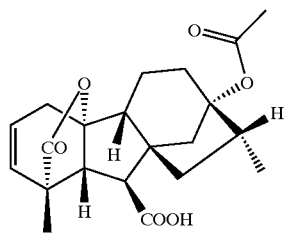

exo-16, 17-Dihydro-GA₅-13-acetate

VII

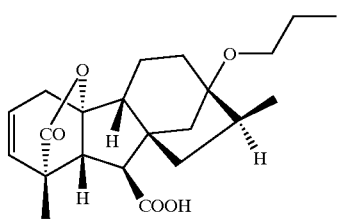

endo-16, 17-Dihydro-GA₅-13-n-propyl ether

VIII

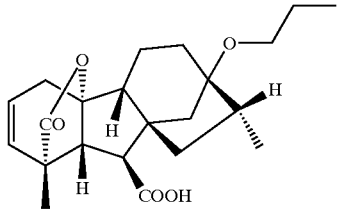

exo-16, 17-Dihydro-GA₅-13-n-propyl ether

IX

The content of the component a) in the inventive formulations is in the range of from 0.1 to 20, in particular 0.2 to 10% by weight of the formulation.

As component b) the inventive formulations contain b) up to 99.9% by weight of an formulation additive selected from the group consisting of b1) the reaction products of triglycerides based on carboxylic acids having 2 to 30 carbon atoms and ethylene oxide and/or propylene oxide in the presence of a base, and/or b2) fatty acid esters of sugar alcohol polyethoxylates.

The component b1 is obtainable by the reaction of an oil/fat based on a triglyceride of carboxylic acids having 2 to 30 carbon atoms and ethylene oxide and/or propylene oxide in the presence of a base. Fatty acid alkoxylates are primarily formed.

In the triglycerides, three equivalents of carboxylic acid are esterified with glycerol. The carboxylic acids can be saturated or mono- or polyethylenically unsaturated.

Preferably, the present invention uses naturally occurring oils and fats which contain triglycerides as the main constituent. They can be crude, denatured or refined.

Suitable natural oils and fats are: vegetable oils such as olive oil, safflower oil, soybean oil, groundnut oil, cotton oil, corn oil, rape oil, castor oil, sunflower oil, coffee oil, linseed oil, coconut fat and mixtures thereof, animal fats and oils such as fish oils, e.g. sardine oil, herring oil, salmon oil, shark-liver oil or whale oil, and further tallow oil, bone oil, woolfat fractions and bovine tallow.

The following vegetable oils are preferred: castor oil, soybean oil, rape oil and corn oil. Particularly preferred of these is castor oil.

Per mol of the triglyceride on which the oil is based, from 1 to 100, preferably from 10 to 35 and in particular from 15 to 30, mol of ethylene oxide and/or propylene oxide are employed.

Suitable bases are especially inorganic bases such as the alkali metal or alkaline earth metal hydroxides, e.g. sodium hydroxide, potassium hydroxide or calcium hydroxide. Instead of the direct use of hydroxides, it is possible to use carbonates or hydrotalcites, which, if appropriate, were hydrophobized with aliphatic or aromatic carboxylic acids, alcohols having 4 to 22 carbon atoms or the ethoxylates of alcohols of this type, or basic alkaline earth metal phosphates such as strontium phosphate, barium phosphate and calcium phosphate, each of which also form hydroxide ions in the presence of small amounts of water.

The base particularly used is potassium hydroxide.

Per mol of triglyceride, from 0.1 to 5, and in particular from 0.1 to 2, % by weight of base, based on the weight of the triglyceride, are generally added to the reaction mixture.

The reaction is generally carried out at elevated pressure, preferably at from 1 to 10 and in particular at from 1 to 5 bar and at from 80 to 230 and especially from 100 to 150° C.

Working-up is in general carried out such that excess ethylene oxide or propylene oxide is removed under reduced pressure.

Otherwise, the carrying-out of such alkoxylation reactions and the isolation of the resulting reaction products is known to the person skilled in the art (cf. N. Schönfeldt, Grenzflächenaktive Ethylenoxidaddukte [Surface-active ethylene oxide adducts], Wissenschaftliche Verlagsgesellschaft mbH, Stuttgart, 1984).

A particularly preferred product for component b1 is the product obtainable by the reaction of an oil/fat based on a triglyceride of carboxylic acids having 10 to 20 carbon atoms and 10 to 30 mol equivalents of ethylene oxide and/or propylene oxide in the presence of hydroxide ions.

Preferred as component b2 are the esters derived from $C_8$–$C_{28}$ fatty acids with $C_5$- and/or $C_6$ sugar alcohol polyethoxylates comprising preferably of from 10 to 100, particularly 20 to 50 ethoxylate units.

Preferred fatty acids are oleic acid, stearic acid, pelargonic acid and 2-Ethylhexanoic acid or mixtures thereof.

Component b can be solely constituted of component b1 or b2 or of mixtures of both species.

Component b constitutes up to 99.9, preferably 0.5 to 50, in particular 0.5 to 25% by weight of the formulations in accordance with the instant invention.

The formulations according to the invention can moreover additionally contain further customary additives such as surfactants, antifoams, cosolvents, etc.

Suitable surfactants are:

anionic surfactants, e.g. alkali metal, alkaline earth metal or ammonium salts of the fatty acids such as potassium stearate, alkylsulfates, alkyl ether sulfates, alkyl- or isoalkylsulfonates, alkylbenzenesulfonates such as Na dodecylbenzenesulfonates, alkylnaphthalenesulfonates, alkylmethyl ester sulfonates, acylglutamates, alkylsuccinic acid ester sulfonates, sarcosinates such as sodium lauroyl sarcosinate or taurates, cationic surfactants, e.g. alkyltrimethylammonium halides or alkylsulfates, alkylpyridinium halides or dialkyldimethylammonium halides or alkylsulfates, nonionic surfactants, e.g. alkoxylated animal or vegetable fats and oils such as corn oil ethoxylates, castor oil ethoxylates, tallow fat ethoxylates, glycerol esters such as glycerol monostearate, fatty alcohol alkoxylates and oxo-alcohol alkoxylates, fatty acid alkoxylates such as oleic acid ethoxylates, alkylphenyl alkoxylates such as isononylphenol ethoxylates, fatty amine alkoxylates, fatty acid amide alkoxylates, sugar surfactants such as sorbitan fatty acid esters (sorbitan monooleate, sorbitan tristearate), polyoxyethylenesorbitan fatty acid esters, alkyl polyglycosides, N-alkylgluconamides, alkylmethyl sulfoxides, alkyldimethylphosphine oxides such as tetradecyldimethylphosphine oxide, zwitterionic surfactants, e.g. sulfobetaines, carboxybetaines, alkyldimethylamine oxides such as tetradecyldimethylamine oxide, polymer surfactants, e.g. di-, tri- or multi-blockpolymers of the type $(AB)_x$, ABA and BAB such as polyethylene oxide-block-polypropylene oxide, polystyrene-block-polyethylene oxide, AB comb polymers such as polymethacrylate or polyacrylate comb-polyethylene oxide, perfluoro surfactants, silicone surfactants, phospholipids such as lecithin, amino acid surfactants such as N-lauroyl glutamate, surface-active homo- and copolymers such as polyvinylpyrrolidone, polyacrylic acid, polyvinyl alcohol, polyethylene oxide, maleic anhydride-isobutene copolymers, vinylpyrrolidone-vinyl acetate copolymers.

Preferably, the surfactant used is one or more homogeneous or mixed esters of phosphoric acid or diphosphoric acid with polyalkylene oxide ethers, the polyalkylene oxide ethers generally having only a single hydroxyl group (e.g. Klearfac®, manufacturer: BASF Corp.).

Suitable polyalkylene oxide ethers are, for example, ethers of alkylphenols such as nonylphenol or of branched or unbranched aliphatic alcohols, for example having 6 to 30, preferably having 10 to 20, carbon atoms and in particular of fatty alcohols having 10 to 12 carbon atoms.

The monohydroxylated polyalkylene oxide ethers are generally known or accessible in a manner known per se, especially by alkoxylation of the corresponding alcohols. Preferred alkoxylating agents are ethylene oxide and propylene oxide, which can be reacted with a suitable phosphorus compound individually, in a mixture, in succession or alternately, by means of which alkoxylation products of differing composition, for example having block structures, can result.

The preparation of these phosphoric acid esters is generally known and is carried out, for example, by reaction of the corresponding monofunctional polyalkylene oxide ether with phosphoric acid, diphosphorus pentoxide, polyphosphoric acid or phosphorus oxytrichloride (cf. "Nonionic Surfactants", Martin Schick (Ed.), Marcel Dekker, New York, 1964, Chapter 11, pages 372–394).

The proportion of the surfactants can be from 0 to 30, preferably from 2 to 15, % by weight.

Suitable antifoams are aliphatic or aromatic monoalcohols having 4 to 14, preferably 6 to 10, carbon atoms, such as n-octanol or n-decanol or silicone surfactants.

The proportion of the antifoams in the mixture is normally from 0.5 to 15 and especially from 3 to 8% by weight.

Suitable cosolvents are mineral oils, naturally occurring oils such as rape oil, soybean oil and the methyl esters of carboxylic acids on which these oils are based, such as methyl oleate and rape oil methyl ester, fatty acid esters, especially with $C_1$–$C_4$-alkanols and organic solvents such as benzenes or naphthalenes substituted by straight-chain or branched alkyl groups (Shellsol 150®, Shellsol 200® and Solvesso® brands).

The proportion of the cosolvents in the mixture can be from 1 to 60 and especially from 5 to 30% by weight.

Furthermore, the mixture can contain from 0 to 15 and especially from 2 to 10% by weight of water.

Additionally, the mixture can contain one or more carboxylic acids having from 4 to 20, in particular from 6 to 18, carbon atoms such as oleic acid or 2-ethylhexanoic acid and/or one or more of the dicarboxylic acids on which the compounds I are based, e.g. adipic acid, sebacic acid or succinic acid.

The proportion of these (di)carboxylic acids in the mixture is from 0 to 30, preferably from 0 to 10, % by weight.

As component d) the plant growth regulating formulations in accordance with the instant invention can additionally contain further known plant growth regulating compounds.

The biological activity of 16,17-dihydro GAs can be improved in a synergistic manner (cf. S. R. Colby, Weeds 25: 20–22) by co-applying them with other plant growth regulators. This is particularly observed when using the preferred compounds VI or VII in formulations or spray solutions in combination with other growth retardants, i.e. compounds leading to a reduction of shoot length.

Plant growth retardants of practical relevance are, for instance, ethephon (standard compound I), the quaternary ammonium compounds chlormequat chloride (standard compound II)

mepiquat chloride (standard compound III), compounds possessing a N-containing heterocycle ancymidol flurprimidol paclobutrazol uniconazole-P inabenfide, the acylcyclohexanediones prohexadione-Ca (standard compound IV)

trinexapac-ethyl (standard compound V)

16,17-dihydro GAs are also suitable to synergize the biological activity of exogenously applied gibberellins, such as gibberellic acid ($GA_3$=compound VI) or other GAs with immediate biological activity (e.g. $GA_4$, $GA_7$). The commercially available $GA_3$ and $GA_{4+7}$ have found a large number of applications [for details see Thomson, W. H. (1995) Agricultural Chemicals, Book III, Thomson Publications, Fresno, USA, p. 29–35].

Particularly in graminaceous species, the preferred compounds VI and VII synergize the action of exogenously applied GAs and can, thus, be used to increase the yield of malt and decrease the amount of time required for the malting process in the brewing industry increase the yield of sugar cane stimulate germination and seedling development in rice, wheat, barley, oats, rye, maize, sorghum, turf grasses and other plant species.

In addition to enhancing the biological performance of 16,17-dihydro-GAs by using suitable adjuvants for the preparation of formulations, additional optimisation can be achieved by adding further adjuvants to the spray solution (tank mixing). Particularly preferred adjuvants are ammonium sulphate or citric acid added at a concentration of from 0.01 to 0.5% by weight, preferably 0.05 to 0.2% by weight.

EXAMPLES

Unless otherwise noted, the growth regulating proerties of different compounds in different formulations were determined under greenhouse conditions as follows:

Test plants were grown in plastic pots of approximately 12.5 cm in diameter in a substrate provided with sufficient nutrients and water. At an appropriate shoot length the plants were treated with aqueous sprays of the formulations. The growth-regulating action observed was confirmed at the end of the experiment by measuring the height of the plants. The results obtained were compared with the growth height of the untreated plants.

In cases in which a reduction in growth height was achieved, a deeper leaf coloration could be observed. The increased chlorophyll content is indicative of an increased rate of photosynthesis, making for bigger yields.

A. Finding of the Most Preferred Compounds

Example 1 Shoot Length Reduction in Small Grains and Rice*

| Compound | Structure | Shoot length reduction [activity, relative to control] in | | | | |
|---|---|---|---|---|---|---|
| | | wheat | barley | oats | rye | rice |
| Comp. II | exo-16,17-Dihydro-$GA_5$ | +<br>(+) | + | 0 | ++<br>(+) | / |
| Comp. III | endo-16,17-Dihydro-$GA_5$ | ++ | ++ | 0 | +++ | / |
| Comp. IV | Dichloromethano-16,17-dihydro-$GA_5$ | + | ++ | + | ++ | / |
| Comp. V | Dichloromethano-16,17-dihydro-$GA_5$-13-acetate | 0 | 0 | + | + | / |
| Comp. VI | endo-16,17-Dihydro-$GA_5$-13-acetate | +++ | +++ | ++<br>(+) | +++ | +++ |
| Comp. VII | exo-16,17-Dihydro-$GA_5$-13-acetate | +++ | +++ | +++ | +++ | +++ |
| Comp. IX | exo-16,17-Dihydro-$GA_5$-13-n-propyl ether | ++<br>(+) | ++<br>(+) | ++ | ++ | ++ |

*1% formulations in cyclohexanone: Emulan EL = 4:1
0 = no effect,
+ = low activity,
++ = intermediate activity
+++ = high activity,
/ = not tested In order to obtain results equivalent to compounds VI, VII, and IX in these plant species, dosages approximately 20 times higher have to be used of the standard compounds S1 (ethephon), S4 (prohexadione-Ca) or S5 (trinexapac-ethyl) applied in commercial formulations. In wheat, standard compounds S2 and S3 require dosages of the respective active ingredients approximately 100 times higher. (Standard compounds S2 and S3 are significantly less active in the other plant species.)

Example 2 Shoot Length Reduction in Wheat and Barley*

| Compound | Rate [g/ha ai] | Shoot length | |
|---|---|---|---|
| | | Wheat [% of control] | Barley [% of control] |
| Comp. IV | 1.6 | 99 | 99 |
| | 3.1 | 95 | 100 |
| | 6.3 | 92 | 98 |

-continued

|  | Rate | Shoot length | |
|---|---|---|---|
| Compound | [g/ha ai] | Wheat [% of control] | Barley [% of control] |
|  | 12.5 | 83 | 87 |
| Comp. V | 1.6 | 101 | 99 |
|  | 3.1 | 95 | 97 |
|  | 6.3 | 84 | 82 |
|  | 12.5 | 75 | 76 |
| Comp. VI | 1.6 | 88 | 95 |
|  | 3.1 | 88 | 84 |
|  | 6.3 | 68 | 65 |
|  | 12.5 | 64 | 53 |
| Comp. VII | 1.6 | 90 | 97 |
|  | 3.1 | 73 | 78 |
|  | 6.3 | 70 | 61 |
|  | 12.5 | 64 | 57 |

*1% formulations in Atlas G 1086 were used.

The results of Examples 1 and 2 demonstrate that compounds VI, VII, and IX are superior to compounds II to V.

Examples 3 and 4

Comparison of the plant growth-retarding activity of Compound VII using distinct adjuvants for the preparation of spray solutions or formulations.

Assays with wheat, barley, oat, and rye plants were carried out as described above. The aqueous spray solutions were prepared as follows:

A Spray solution containing 5% ethanol (cf. PCT/AU95/00528, Example 39).
B Spray solution containing 5% ethanol and 0.1% Agral 90 (cf. PCT/AU95/95/00426, Example 40).
C Spray solution containing 10% ethanol and 0.1% Silwett L 477 (cf. PCT/AU92/00426, Example 11).
D Spray solution prepared from a 1% formulation of Compound VII in cyclohexanone:Emulan EL ( BASF AG, Ludwigshafen, Germany)=4:1.
E Spray solution prepared from a 1% formulation of Compound VII in Atlas G 1086 (ICI Surfactants, Fernhurst, Haslemere,Surrey GU27 3JE, GB)
F Spray solution prepared from a 1% formulation of Compound VII in ethoxylated castor oil R 15

Example 3

| Preparation of spray solution | Compound VII [g/ha ai] | Shoot length [% of control] | |
|---|---|---|---|
|  |  | Barley | Wheat |
| A | 1.5 | 92 | 95 |
|  | 3.0 | 89 | 95 |
|  | 6.0 | 94 | 90 |
|  | 12.0 | 88 | 85 |
| B | 1.5 | 89 | 87 |
|  | 3.0 | 79 | 80 |
|  | 6.0 | 76 | 79 |
|  | 12.0 | 73 | 78 |
| C | 1.5 | 83 | 87 |
|  | 3.0 | 82 | 86 |
|  | 6.0 | 79 | 79 |
|  | 12.0 | 74 | 79 |
| D | 1.5 | 92 | 91 |
|  | 3.0 | 82 | 83 |
|  | 6.0 | 76 | 82 |

-continued

| Preparation of spray solution | Compound VII [g/ha ai] | Shoot length [% of control] | |
|---|---|---|---|
|  |  | Barley | Wheat |
|  | 12.0 | 71 | 79 |
| F | 1.5 | 85 | 85 |
|  | 3.0 | 82 | 83 |
|  | 6.0 | 71 | 79 |
|  | 12.0 | 68 | 75 |

As can be seen from Examples 3 and 4, the biological performance of 16,17-dihydro GAs can be particularly enhanced if adjuvants such as Emulan EL, Atlas G 1086 or ethoxylated castor oil R 15 are used for formulation.

Example 5

Specific improvement of the biological performance of 16,17-dihydro GAs by ethoxylated castor oil R 15 (R 15)

| Active Ingredient | Rate [g/ha ai] | Adjuvant | Rate [g/ha ai] | Shoot length [% of control] | |
|---|---|---|---|---|---|
|  |  |  |  | Barley | Wheat |
| — | — | Ethanol | 500 | 100 | 100 |
| — | — | R 15 | 500 | 99 | 98 |
| Compound VII | 2.5 | Ethanol | 500 | 99 | 99 |
| Compound VII | 2.5 | R 15 | 500 | 75 | 73 |
| Standard Compound S1 | 250 | — | — | 95 | 93 |
| Standard Compound S1 | 250 | R 15 | 500 | 101 | 92 |
| Standard Compound S2 | 750 | — | — | 94 | 83 |
| Standard Compound S2 | 750 | R 15 | 500 | 94 | 75 |

The results contained in Example 5 demonstrate that there is a specific and surprising interaction between the 16,17-dihydro GAs and these formulation components since such activity-enhancing effects are not or only at a far lower degree found if equivalent experiments are carried out using standard compounds S1 or S2, respectively.

Example 6 Synergistic Combinations

To show the synergistic effects of formulations in accordance with the instant invention together with further growth regulating agents, formulations in accordance with the invention were prepared and additional active ingredients added.

The results are given in the following tables.

Shoot height reduction in spring barley (cv. "Alexis") 20 days after treatment with combinations of standard compound S2 and compound VII

| Compound | Rate [g/ha a.i.] | % Shoot height reduction | | |
|---|---|---|---|---|
|  |  | Actual | Expected | Synergism? |
| S2 | 750 | 11 | / | / |
| S2 | 1500 | 10 | / | / |
| VII | 3 | 6 | / | / |
| VII | 6 | 18 | / | / |

-continued

| Compound | Rate [g/ha a.i.] | % Shoot height reduction | | Synergism? |
|---|---|---|---|---|
| | | Actual | Expected | |
| S2 + VII | 750 + 3 | 14 | 16 | + |
| S2 + VII | 750 + 6 | 40 | 27 | + |
| S2 + VII | 1500 + 3 | 20 | 15 | + |
| S2 + VII | 1500 + 6 | 40 | 26 | + |

Shoot height reduction in spring wheat (cv. "Ralle") 21 days after treatment with combinations of standard compound S4 and compound VII

| Compound | Rate [g/ha a.i.] | % Shoot height reduction | | Synergism? |
|---|---|---|---|---|
| | | Actual | Expected | |
| S4 | 30 | 6 | / | / |
| S4 | 60 | 15 | / | / |
| VII | 3 | 8 | / | / |
| VII | 6 | 21 | / | / |
| S4 + VII | 30 + 3 | 16 | 14 | (+) |
| S4 + VII | 30 + 6 | 33 | 26 | + |
| S4 + VII | 60 + 3 | 42 | 22 | + |
| S4 + VII | 60 + 6 | 49 | 33 | + |

Shoot height reduction in spring barley (cv. "Alexis") 20 days after treatment with combinations of standard compound S4 and compound VII

| Compound | Rate [g/ha a.i.] | % Shoot height reduction | | Synergism? |
|---|---|---|---|---|
| | | Actual | Expected | |
| IV | 30 | 10 | / | / |
| IV | 60 | 27 | / | / |
| 6 | 3 | 6 | / | / |
| 6 | 6 | 18 | / | / |
| S4 + VII | 30 + 3 | 29 | 15 | + |
| S4 + VII | 30 + 6 | 45 | 26 | + |
| S4 + VII | 60 + 3 | 39 | 31 | + |
| S4 + VII | 60 + 6 | 47.5 | 40 | + |

Shoot height reduction in spring wheat (cv. "Ralle") 13 days after treatment with combinations of standard compound S5 and compound VII

| Compound | Rate [g/ha a.i.] | % Shoot height reduction | | Synergism? |
|---|---|---|---|---|
| | | Actual | Expected | |
| S5 | 30 | 14 | / | / |
| VII | 6 | 18 | / | / |
| S5 + VII | 30 + 6 | 32 | 17 | + |

16,17-dihydro GAs are also suitable to synergize the biological activity of exogenously applied gibberellins, such as gibberellic acid ($GA_3$=standard compound S6) or other GAs with immediate biological activity (e.g. $GA_4$, $GA_7$). The commercially available $GA_3$ and $GA_{4+7}$ have found a large number of applications [for details see Thomson, W. H. (1995) Agricultural Chemicals, Book III, Thomson Publications, Fresno, USA, p. 29–35].

Particularly in graminaceous species, the preferred compounds VI and VII synergize the action of exogenous GAs and can, thus, be used to increase the yield of malt and decrease the amount of time required for the malting process in the brewing industry increase the yield of sugar cane stimulate germination and seedling development in rice, wheat, barley, oats, rye, maize, sorghum, turf grasses and other plant species.

The synergizing effect of compound VII on shoot elongation in rice is shown in the results of Example 7. The shoot growth-promoting effect of $GA_3$ could clearly be raised by compound VII which, applied alone, reduces shoot elongation.

Example 7

Enhanced shoot growth of rice seedlings [cvs. "Koshihikari" tall), "Tan-ginbozu" (dwarf), "Waito C" (dwarf)] 7 days after treatment with combinations of compound 6 with $GA_3$[d]

| Compound(s) | Rate [g/ha ai] | Koshihikari [% of Control][a] | Tan-ginbozu [% of Control][b] | Waito C [% of Control][c] |
|---|---|---|---|---|
| VII | 12.5 | 75 | 74 | 80 |
| VII | 25.0 | 75 | 74 | 80 |
| VII | 50.0 | 75 | 74 | 80 |
| S6 | 1.25 | 109 | 128 | 115 |
| S6 | 2.50 | 112 | 160 | 143 |
| S6 | 5.00 | 124 | 186 | 190 |
| VII | 12.5 | 118 | 170 | 167 |
| S6 | 1.25 | | | |
| VII | 12.5 | 132 | 191 | 195 |
| S6 | 2.50 | | | |
| VII | 12.5 | 147 | 229 | 230 |
| S6 | 5.00 | | | |
| VII | 25.0 | 129 | 197 | 184 |
| S6 | 1.25 | | | |
| VII | 25.0 | 141 | 223 | 207 |
| S6 | 2.50 | | | |
| VII | 25.0 | 149 | 229 | 230 |
| S6 | 5.00 | | | |
| VII | 50.0 | 129 | 202 | 184 |
| S6 | 1.25 | | | |
| VII | 50.0 | 135 | 213 | 218 |
| S6 | 2.50 | | | |
| VII | 50.0 | 155 | 234 | 253 |
| S6 | 5.00 | | | |

[a]100% = 17.4 cm/shoot length at foliar treatment: 12.5 cm
[b]100% = 9.4 cm/shoot length at foliar treatment: 6.0 cm
[c]100% = 8.7 cm/shoot length at foliar treatment: 5.0 cm
[d]1 kg/ha of ammonium sulphate added to the spray solution

What is claimed is:

1. A plant growth regulating composition comprising
a) 0.1 to 20% by weight of a 16,17-dihydro gibberellin of general formulae Ia or Ib

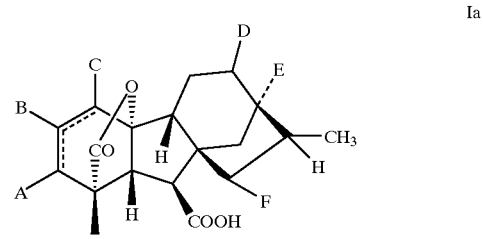

Ia wherein A, B, C, D, E and F independently represent hydrogen atoms or hydroxyl groups and the dotted line represents one optional double bond either between the carbon atoms in position 1 and 2 or between the carbon atoms in positions 2 and 3, and

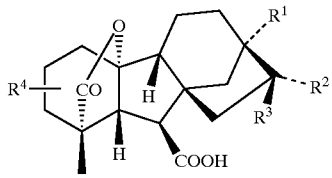

wherein
$R^1$ represents H or OH, OC(=O)$R^5$ or O$R^5$
$R^2$, $R^3$, which may be the same or different, each represent H, F, Cl, Br, lower ($C_{1-6}$) alkyl, lower ($C_{2-6}$) alkenyl, lower ($C_{3-6}$) cycloalkyl, or CH$_2$X (wherein X is F, Cl or Br);
$R^4$ indicates that the A ring may be (i) unfunctionalised, or (ii) contain a 1,2-double bond or 2,3-double bond, or (iii) contain a 3α- or 3β-OH, F, Cl or Br group with or without a 1,2-double bond, or (iv) contain a 1α- or 1β-OH, F Cl or Br group with or without a 2,3-double bond;
$R^5$ represents $C_1$–$C_6$-alkyl.
b) 0.5 to 99.9% by weight of an formulation additive selected from the group consisting of
  b1) the reaction products of triglycerides based on carboxylic acids having 2 to 30 carbon atoms and ethylene oxide and/or propylene oxide in the presence of a base, and/or
  b2) fatty acid esters of sugar alcohol polyethoxylates
c) up to 50% by weight of an organic solvent
d) 0.1 to 50% by weight of a formulation auxiliary different from b1 and b2,
e) up to 50% by weight of additional plant growth regulating compounds.

2. The plant growth regulating composition defined in claim 1, wherein component (a) comprises one or more compounds selected from the group consisting of exo-16,17-dihydro-GA$_5$-13-acetate, endo-16,17-dihydro-GA$_5$-13-acetate, exo-16,17-dihydro-GA$_5$-13-$C_1$–$C_4$-alkyl ether and endo-16,17-dihydro-GA$_5$-13-$C_1$–$C_4$-alkyl ether.

3. The plant growth regulating composition defined in claim 1, wherein component (b) is a compound b1.

4. The plant growth regulating composition defined in claim 1, wherein component (b) is a compound b2.

5. The plant growth regulating composition defined claim 1, wherein component (e) is one or more compounds selected from the group consisting of chlormequat chloride, mepiquat chloride, prohexadione-Ca, trinexapac ethyl and ethephon.

6. The plant growth regulating composition defined in claim 1, wherein component (e) is GA$_3$ or a mixture of GA$_4$ and GA$_7$.

7. A method of retarding the growth of a plant which comprises treating the plant or its environment with an effective amount of the growth regulating composition defined in claim 1.

8. A method of stimulating shoot growth in graminaceous plant species which comprises treating the plant species or its environment with an effective amount of the plant growth regulating composition defined in claim 6.

* * * * *